(12) United States Patent
Dukes et al.

(10) Patent No.: US 6,586,512 B1
(45) Date of Patent: Jul. 1, 2003

(54) BINDING SUPERABSORBENT POLYMERS TO SUBSTRATES

(75) Inventors: Charles D. Dukes, Midland, MI (US); Donna G. Shaffer, Midland, MI (US)

(73) Assignee: The Dow Chemical Company, Midland, MI (US)

( * ) Notice: Subject to any disclaimer, the term of this patent is extended or adjusted under 35 U.S.C. 154(b) by 250 days.

(21) Appl. No.: 09/675,103

(22) Filed: Sep. 28, 2000

Related U.S. Application Data

(60) Provisional application No. 60/156,782, filed on Sep. 30, 1999.

(51) Int. Cl.$^7$ .............................. C08J 5/10; C08K 5/06; C08L 31/00
(52) U.S. Cl. .................... 524/377; 525/186; 525/187; 525/430; 525/438
(58) Field of Search .................... 524/377; 525/186, 525/187, 430, 438

(56) References Cited

U.S. PATENT DOCUMENTS

| | | | | |
|---|---|---|---|---|
| 3,305,528 | A | 2/1967 | Wynstra et al. ............... | 260/47 |
| 3,669,103 | A | 6/1972 | Harper et al. ............... | 128/156 |
| 3,670,731 | A | 6/1972 | Harmon ..................... | 128/284 |
| 3,926,891 | A | 12/1975 | Gross et al. ............. | 260/29.6 E |
| 3,935,099 | A | 1/1976 | Weaver et al. ............... | 210/43 |
| 3,941,858 | A | 3/1976 | Shepherd et al. ........... | 260/885 |
| 3,997,484 | A | 12/1976 | Weaver et al. ........ | 260/17.4 GC |
| 4,048,141 | A | 9/1977 | Doorakian et al. ........... | 260/47 |
| 4,076,663 | A | 2/1978 | Masuda et al. ....... | 260/17.4 GC |
| 4,090,013 | A | 5/1978 | Ganslaw et al. ............... | 526/15 |
| 4,093,776 | A | 6/1978 | Aoki et al. .................. | 428/402 |
| 4,171,420 | A | 10/1979 | Doorakian et al. ........... | 528/89 |
| 4,190,562 | A | 2/1980 | Westerman .......... | 260/17.4 UC |
| 4,286,682 | A | 9/1981 | Stewart et al. .......... | 180/9.24 A |
| 4,338,371 | A | 7/1982 | Dawn et al. ................ | 428/283 |
| 4,340,706 | A | 7/1982 | Obayashi et al. ............ | 526/207 |
| 4,430,086 | A | 2/1984 | Repke ......................... | 604/385 |
| 4,446,261 | A | 5/1984 | Yamasaki et al. ............. | 524/40 |
| 4,459,396 | A | 7/1984 | Yamasaki et al. ........... | 526/200 |
| 4,500,315 | A | 2/1985 | Pieniak et al. ............... | 604/379 |
| 4,537,590 | A | 8/1985 | Pienial et al. ............... | 604/379 |
| 4,596,567 | A | 6/1986 | Iskra ......................... | 604/368 |
| 4,610,678 | A | 9/1986 | Weisman et al. ........... | 604/368 |
| 4,654,039 | A | 3/1987 | Brandt et al. ............... | 604/368 |
| 4,673,402 | A | 6/1987 | Weisman et al. ........... | 604/368 |
| 4,676,784 | A | 6/1987 | Erdman et al. ............. | 604/368 |
| 4,683,274 | A | 7/1987 | Nakamura et al. ........... | 526/216 |
| 4,708,997 | A | 11/1987 | Stanley, Jr. et al. ........ | 526/207 |
| 4,795,454 | A | 1/1989 | Dragoo .................... | 604/285.2 |
| 4,798,603 | A | 1/1989 | Meyer et al. ............... | 604/378 |
| 4,857,610 | A | 8/1989 | Chmelir et al. ............... | 526/88 |
| 4,892,598 | A | 1/1990 | Stevens et al. ............... | 156/91 |
| 4,935,022 | A | 6/1990 | Lash et al. ................. | 604/368 |
| 4,938,756 | A | 7/1990 | Salek ......................... | 604/368 |
| 4,973,325 | A | 11/1990 | Sherrod et al. ............. | 604/368 |
| 4,985,518 | A | 1/1991 | Alexander et al. .......... | 526/240 |
| 5,061,259 | A | 10/1991 | Goldman et al. ............ | 604/368 |
| 5,089,588 | A | 2/1992 | White et al. .................. | 528/99 |
| 5,134,218 | A | 7/1992 | Brennan et al. ............... | 528/99 |
| 5,143,998 | A | 9/1992 | Brennan et al. ............... | 528/99 |
| 5,145,906 | A | 9/1992 | Chambers et al. .......... | 524/732 |
| 5,147,343 | A | 9/1992 | Kellenberger ............... | 604/368 |
| 5,149,335 | A | 9/1992 | Kellenberger et al. ...... | 604/372 |
| 5,149,768 | A | * | 9/1992 | White et al. .................. | 528/89 |
| 5,164,472 | A | 11/1992 | White et al. .................. | 528/97 |
| 5,171,820 | A | 12/1992 | Mang et al. .................. | 528/87 |
| 5,275,853 | A | * | 1/1994 | Silvis et al. ................ | 428/35.4 |
| 5,364,382 | A | 11/1994 | Latimer et al. ............. | 604/378 |
| 5,401,814 | A | 3/1995 | Schomaker et al. ........ | 525/523 |
| 5,429,629 | A | 7/1995 | Latimer et al. ............. | 604/378 |
| 5,486,166 | A | 1/1996 | Bishop et al. ............. | 604/366 |
| 5,496,910 | A | 3/1996 | Mang et al. .................. | 528/88 |
| 5,520,673 | A | 5/1996 | Yarbrough et al. ......... | 604/378 |
| 5,531,728 | A | 7/1996 | Lash .......................... | 604/378 |
| 5,562,646 | A | 10/1996 | Goldman et al. ........... | 604/368 |
| 5,728,082 | A | 3/1998 | Gustafsson et al. ......... | 604/368 |
| 6,011,111 | A | * | 1/2000 | Brennan et al. ............ | 524/601 |
| 6,407,225 | B1 | * | 6/2002 | Mang et al. ............. | 536/123.1 |

FOREIGN PATENT DOCUMENTS

| | | |
|---|---|---|
| DE | 232058 A1 | 1/1986 |
| EP | 2627080 A1 | 2/1988 |
| EP | 0401189 B2 | 5/1990 |
| EP | 0558889 B2 | 5/1990 |
| EP | 0640330 B1 | 12/1993 |
| EP | 0670154 B1 | 3/1995 |
| EP | 0719531 A1 | 12/1995 |
| WO | WO 91/11163 | 8/1991 |
| WO | WO 91/18042 | 11/1991 |
| WO | WO 92/11831 | 7/1992 |
| WO | WO 95/00183 | 1/1995 |
| WO | WO 95/01146 | 1/1995 |
| WO | WO 95/22358 | 8/1995 |
| WO | WO 95/26209 | 10/1995 |
| WO | WO 97/12575 | 4/1997 |
| WO | WO 97/13484 | 4/1997 |
| WO | WO 97/34558 | 9/1997 |
| WO | WO 98/06364 | 2/1998 |
| WO | WO 98/22065 | 5/1998 |
| WO | WO 98/22066 | 5/1998 |
| WO | WO 98/22067 | 5/1998 |
| WO | WO 98/51251 | 11/1998 |
| WO | WO 00/26319 | 5/2000 |

OTHER PUBLICATIONS

Reinking, Barnabeo, and Hale Journal of Applied Polymer Science, vol. 7, p. 2135 (1963).

* cited by examiner

Primary Examiner—James J. Seidleck
Assistant Examiner—U. K Rajguru
(74) Attorney, Agent, or Firm—Paul D. Hayhurst

(57) ABSTRACT

A composition comprising a superabsorbent polymer and a hydroxy-functionalized polyether.

39 Claims, No Drawings

BINDING SUPERABSORBENT POLYMERS TO SUBSTRATES

This application claims the benefit of U.S. Provisional Application No. 60/156,782, filed Sep. 30, 1999.

BACKGROUND OF THE INVENTION

The present invention relates to superabsorbent polymer compositions and their use in absorbent articles.

Superabsorbent polymers are well-known materials that commonly are used in personal care articles such as diapers. These polymers are known to absorb several times their weight of, for example, water, saline solution, urine, blood, and serous bodily fluids. Fixation or containment of superabsorbent polymer particles within an absorbent device is important to producers of absorbent personal-care devices. This containment reduces particle shakeout in these devices. Particle shakeout can result in loss of containment of the particle in the device and subsequent contact of the particle with a user's skin. Particle shakeout also results in redistribution of the particles within the device, potentially causing performance problems with the device.

It would be desirable to have an improved solution to the problem of particle shakeout in personal-care devices, cable wrap components, and other applications where particle shakeout is a problem.

SUMMARY OF THE INVENTION

The present invention includes such a solution in the form of a process comprising contacting a substrate with a superabsorbent polymer and a binding amount of a hydroxy-functionalized polyether. This process reduces the shakeout of a superabsorbent polymer from an absorbent article. In another aspect, the invention is a composition comprising a superabsorbent polymer and a hydroxy-functionalized polyether. Surprisingly, the polyether can be employed at very low concentrations to give good adhesion of the superabsorbent polymer to the substrate. In another embodiment, the polyether is employed as part of a hot-melt adhesive composition further optionally comprising a compatible tackifier, a compatible plasticizer and a compatible diluent.

The compositions of the present invention may be employed in a wide variety of uses known in the art, such as, for example, the assembly or construction of cable wrap components and various disposable absorbent articles, such as sanitary napkins, disposable diapers, hospital gowns, bed pads and the like.

DETAILED DESCRIPTION OF THE INVENTION

The process, composition and article of manufacture of the invention employ a superabsorbent polymer and a hydroxy-functionalized polyether (HFPE).

The polyether advantageously is employed in an amount sufficient to bind the superabsorbent polymer of the invention to a substrate. Preferably, the polyether is employed in an amount that is from 0.01 to 20 weight percent of the total weight of polyether and superabsorbent polymer. More preferably, the amount of polyether is from 0.1 to 10 weight percent, even more preferably the amount is from 0.15 to 4 weight percent, and most preferably the amount of polyether is from 0.25 to 2 weight percent. Preferably, the amount of polyether is at least 0.01 weight percent, based on the weight of polyether and superabsorbent polymer, more preferably is at least 0.1 weight percent, even more preferably is at least about 0.15 weight percent, and most preferably is at least 0.25 weight percent. Preferably, the amount of polyether is at most 20 weight percent, based on the weight of polyether and superabsorbent polymer, more preferably is at most 10 weight percent, even more preferably is at most 4 weight percent, and most preferably is at most 2 weight percent. The polyether preferably is thermoplastic.

The polyether employed in the composition of the present invention may be employed in any form such as, for example, neat, or formulated as part of a hot melt adhesive, or as a latex, a suspension, or a fiber, including a multicomponent fiber, or in particulate form, or as mixture of these forms.

Preferably, the HFPE comprises any one of the following hydroxy-functional polyethers:

(1) poly(hydroxy-ethers) polymers having repeating units represented by the formula:

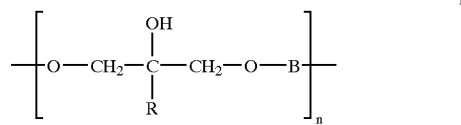

I (2) poly(hydroxy amino ethers) having repeating units represented by the formula:

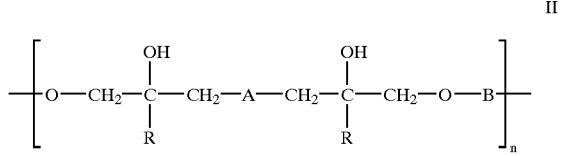

II (3) poly(hydroxy ether sulfonamides) having repeating units represented by the formula:

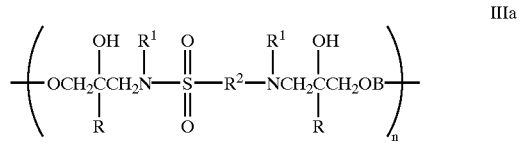

IIIa or

IIIb (4) poly(hydroxy ether sulfides) having repeating units represented by the formula:

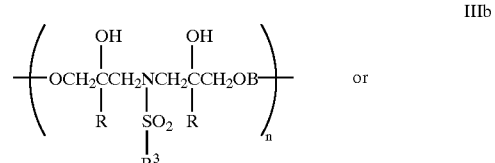

IV (5) poly(hydroxy amide ethers) having repeating units represented independently by any one of the formulas:

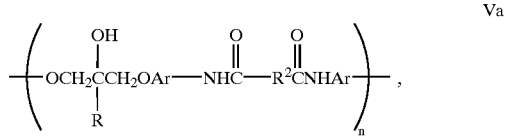

Va

-continued

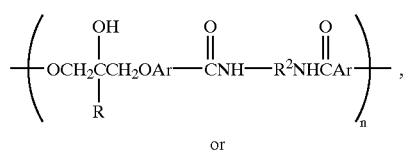
Vb or

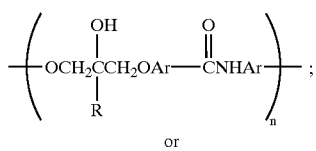
Vc (6) poly(hydroxy amide ethers) having repeating units represented by any one of the formulas:

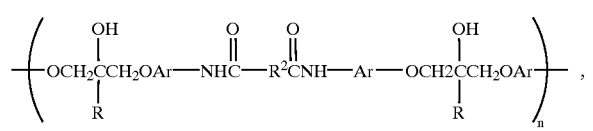
VIa

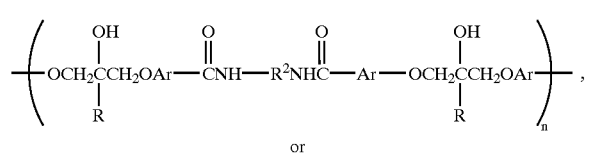
VIb or

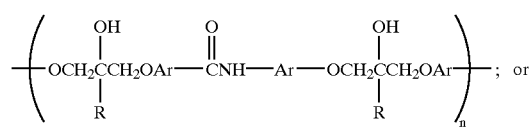
VIc (7) poly(hydroxy ester ethers) or poly(hydroxy esters) having repeating units represented by the formula:

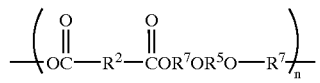
VII wherein $R^5$ is

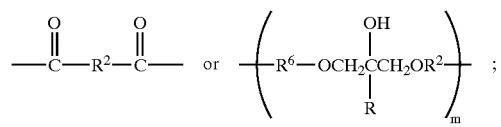

$R^6$ is a divalent organic moiety which is predominantly hydrocarbylene or $R^7$ is

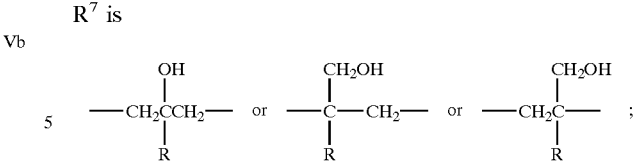

each R independently is alkyl or hydrogen; $R^1$ and $R^3$ are independently a substituted or an unsubstituted alkyl or aryl moiety wherein each substituent independently is a monovalent moiety which is inert in the reactions used to prepare the hydroxy-functionalized polyethers, such as cyano, halo, amido, hydroxy and hydroxyalkyl; each A independently is a diamino moiety or a combination of different amine moieties; each Ar independently is a divalent aromatic moiety; each B, $R^2$, and $R^4$ is independently a divalent organic moiety which is predominantly hydrocarbylene; each $R^8$ independently is methyl or hydrogen; m, x and y are each independently from 0 to 100; and n is an integer from 5 to 1000.

The term "predominantly hydrocarbylene" means a divalent radical which is predominantly hydrocarbon, but which optionally contains a minor amount of one or more heteroatomic moieties such as oxygen, sulfur, imino, sulfonyl, and sulfoxyl.

In the preferred embodiment of the present invention, R is hydrogen; $R^1$ and $R^3$ are independently methyl, ethyl, propyl, butyl, 2-hydroxyethyl or phenyl; Ar, B, $R^2$ and $R^4$ are independently 1,3-phenylene, 1,4-phenylene, sulfonyldiphenylene, oxydiphenylene, thiodiphenylene or isopropylidenediphenylene; and each A independently is 2-hydroxyethylimino, 2-hydroxypropylimino, piperazenyl or N,N'-bis(2-hydroxyethyl)-1,2-ethylenediimino. In one embodiment of the invention, the polyether is not the reaction product of a dicarboxylic acid with a diglycidyl ether.

The hydroxy-functional polyethers having repeating units represented by Formula I are prepared, for example, by contacting a diglycidyl ether or a combination of diglycidyl ethers with a dihydric phenol, such as a bisphenol, or a mixture of dihydric phenols using the process described in U.S. Pat. No. 5,164,472. Alternatively, the poly(hydroxy ethers) are obtained by allowing a dihydric phenol or a combination of dihydric phenols to react with an epihalohydrin by the process described by Reinking, Barnabeo, and Hale in the *Journal of Applied Polymer Science*, Volume 7, page 2135 (1963). Preferably the poly(hydroxy ether) of Formula I is a poly(hydroxy phenoxyether).

The polyetheramines having repeating units represented by Formula II are prepared by contacting one or more of the diglycidyl ethers of a dihydric phenol with a difunctional amine (an amine having two amine hydrogens) under conditions sufficient to cause the amine moieties to react with epoxy moieties to form a polymer backbone having amine linkages, ether linkages and pendant hydroxyl moieties. These polyetheramines are described in U.S. Pat. No. 5,275,853. The polyetheramines can also be prepared by contacting a diglycidyl ether or an epihalohydrin with a difunctional amine.

The hydroxy-functional poly(ether sulfonamides) having repeating units represented by Formulas IIIa and IIIb are

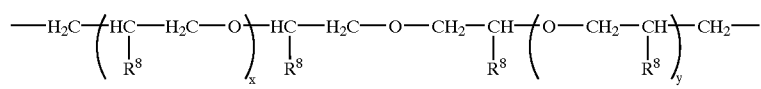

prepared, for example, by polymerizing an N,N'-dialkyl or N,N'-diaryldisulfonamide with a diglycidyl ether as described in U.S. Pat. No. 5,149,768.

The hydroxy-functional polyethers having repeating units represented by Formula IV are prepared by reacting a diglycidyl ether and a dithiol as described in U.S. Pat Nos. 4,048,141 and 4,171,420.

The poly(hydroxy amide ethers) represented by Formula V are prepared by contacting a bis(hydroxyphenylamido) alkane or arene, or a combination of 2 or more of these compounds, such as N,N'-bis(3-hydroxyphenyl)adipamide or N,N'-bis(3-hydroxyphenyl)glutaramide, with an epihalohydrin as described in U.S. Pat. No. 5,134,218.

The poly(hydroxy amide ethers) represented by Formula VI are preferably prepared by contacting an N,N'-bis (hydroxyphenylamido)alkane or arene with a diglycidyl ether as described in U.S. Pat. Nos. 5,089,588 and 5,143,998.

The poly(hydroxy ester ethers) represented by Formula VII are prepared by reacting diglycidyl ethers of aliphatic or aromatic diacids, such as diglycidyl terephthalate, or diglycidyl ethers of dihydric phenols with aliphatic or aromatic diacids such as adipic acid or isophthalic acid. The reaction product is usually and preferably an isomeric mixture of compounds of Formula VII in which each $R^7$ is independently a hydroxy-containing group which results from ring opening of the epoxide groups of the diglycidyl ether or diglycidyl ester, which can give either a pendant hydroxyl group or a pendant hydroxymethyl group. These polyesters are described in U.S. Pat. Nos. 5,171,820 and 5,496,910. Alternatively, the poly(hydroxyester ethers) are prepared by reacting a diglycidyl ester with a bisphenol or by reacting a diglycidyl ester, diglycidyl ether, or an epihalohydrin with a dicarboxylic acid.

The hydroxy-functional polyethers available from Phenoxy Associates, Inc. are also suitable for use in the practice of the present invention. These polymers and the process for preparing them are described in U.S. Pat. Nos. 3,305,528 and 5,401,814.

Optionally, the hydroxy-functionalized polyether has a multimodal molecular weight distribution. The term "multimodal molecular weight distribution," as used herein, means that the base polyether polymer has a molecular weight distribution determined by size exclusion chromatography that contains more than one peak value. The base polymer also can be a mixture of hydroxy-functionalized polyethers of the same or different primary structures with different molecular weights.

When employed in particulate form, hydroxy-functionalized polyether particles are small enough to pass through a 50 mesh sieve (U.S. Sieve Series, 297 micron). Most preferably, hydroxy-functionalized polyether particles preferably are small enough to pass through a 140 mesh sieve (105 micron). The preferred size range, expressed as weight average particle diameter, when the hydroxy-functionalized polyether is in particulate form ranges from 10 to 200 microns, with a more preferred range of from 50 to 150 microns.

In one embodiment of the invention, the polyether is employed as a hot-melt adhesive composition.

The tackifiers which can be employed for preparing the hot-melt adhesive composition include terpene phenolic resins and benzoates, such as, for example, sucrose benzoate. The amount of the tackifier most advantageously incorporated into the hydroxy-functionalized polyether is dependent on a variety of factors including the specific components used to form the hot-melt adhesive composition as well as its desired properties. Typical amounts can range from 0 to 90 weight percent based on the weight of the total composition. Generally, the hot-melt adhesive composition comprises at least 0.1, preferably 1, more preferably 2, and most preferably 4 weight percent and less than 80, preferably 60, more preferably 50 weight percent of the tackifier based on the total weight of the composition.

The plasticizers which can be employed in preparing the hot-melt adhesive composition include phthalate. plasticizers, such as dioctyl phthalate; liquid polyesters such as Dynacol 720 from Hüls; benzoate plasticizers such as diethylene glycol dibenzoate (e.g., Benzoflex 50 available from Velsicol) and diethylene glycol benzoate where the mole fraction of hydroxyl groups which have been esterified ranges from 0.5 to 0.95 (e.g., Benzoflex 2–45 High Hydroxy from Velsicol); phosphate plasticizer such as t-butylphenyl diphenyl phosphate (e.g., Santicizer 154 commercially available from Monsanto); polyalkylene glycols such as the phenyl ether of poly(ethylene glycol) (e.g., Pycal 94 commercially available from ICI); as well as liquid rosin derivatives having Ring and Ball melting points below about 60° C., such as the methyl ester of hydrogenated rosin (e.g., Hercolyn D from Hercules; as well as vegetable and animal oils such as glyceryl esters of fatty acids and polymerization products thereof. If used, the plasticizer is generally present in amounts up to 90 percent by weight, preferably 10 to 40 percent by weight.

Some applications conventionally employing hot-melt adhesives may require the use of wax diluents in order to reduce the melt viscosity or cohesive characteristics of the hot-melt adhesive composition without appreciably decreasing their adhesive bonding characteristics. These waxes are often used in adhesives which do not exhibit pressure sensitive properties. If present, the waxes are used in an amount up to 90 percent by weight, preferably 5 to 35 percent by weight. Suitable waxes include N-(2-hydroxyethyl)-12-hydroxysfearamanide wax, hydrogenated castor oil, oxidized synthetic waxes, poly(ethylene oxide) having a weight average molecular weight of above 1000 and functionalized synthetic waxes such as carbonyl-containing Escomer H 101 from Exxon. Mixtures of one or more of such materials may be employed.

It should be recognized that some adhesive formulations described herein may contain both wax and plasticizer components so that the presence of one or the other is not mutually exclusive.

Other optional additives may be incorporated into the hot-melt adhesive compositions in order to modify certain properties thereof. Among these additives are antioxidants or stabilizers, colorants such as titanium dioxide; and fillers, such as talc and clay. There may also be present in the adhesive composition certain and/or hydrophilic polymers as are conventionally used in this class of adhesive to impart flexibility, toughness, strength and/or water sensitivity. Suitable polymers include ethylene vinyl acetate, ethylene acrylic acid, ethylene methyl acrylate, and ethylene n-butyl acrylate copolymers containing 12 to 50 percent vinyl or acrylate monomers. Suitable hydrophilic polymers include polyvinyl alcohol, hydroxyethyl cellulose, hydroxypropyl cellulose, polyvinyl methyl ether, poly(ethylene oxide), polyvinyl pyrrolidone and the like.

Among the applicable stabilizers or antioxidants which may be included herein are high molecular weight hindered phenols such as sulfur- and phosphorus-containing phenols.

In general, the hot-melt adhesive composition can be prepared using techniques known in the art. An exemplary procedure involves placing approximately 40 percent of the total tackifying resin concentration with all the polyether polymer, wax, plasticizers and stabilizers in a jacketed mixing kettle, preferably in a jacketed heavy duty mixer, which is equipped with rotors and thereupon raising the temperature to a range of up to 190° C. After the resin has melted, the temperature is lowered to 150° C. to 165° C. Mixing and heating are continued until a smooth, homogeneous mass is obtained whereupon the remainder of the tackifying resin is thoroughly and uniformly admixed therewith.

Techniques for melt-blending of a polymer with additives of all types are known in the art. Typically, in a melt blending operation the hydroxy-functionalized polyether is heated to a temperature sufficient to form a polymer melt and combined with the desired amount of the other hot-melt adhesive components in a suitable mixer, such as an extruder, a Banbury mixer, a Brabender mixer, or a continuous mixer. A physical mixture of the different components may also be heated simultaneously and blended using one of the previously mentioned mixers.

The melt blending is preferably carried out in the absence of air, as for example, in the presence of an inert gas, such as argon, neon, or nitrogen; however, it also may be practiced in the presence of air. The melt blending operation can be conducted in a batch or discontinuous fashion but is more preferably conducted in a continuous fashion in one or more processing zones such as in an extruder from which air is largely or completely excluded. The extrusion can be conducted in one zone or step or in a plurality of reaction zones in series or parallel.

A hydroxy-functionalized polyether melt containing the other hot-melt adhesive components may also be formed by reactive melt processing in which the other components are initially dispersed in a liquid or solid monomer or cross-linking agent which will form or be used to form the hot-melt adhesive composition. This dispersion can be injected into a polymer melt containing one or more polymers in an extruder or other mixing device. The injected liquid may result in new polymer or in chain extension, grafting or even cross-linking of the polymer initially in the melt.

The hot-melt adhesive composition can also be formed by mixing the monomer used in forming the hydroxy-functionalized polyether with the other components in the presence or absence of a solvent and subsequently polymerizing the monomer to form the hydroxy-functionalized polyether component of the composition. After polymerization, any solvent that is used is removed by conventional means. Alternatively, the hydroxy-functionalized polyether polymer may be granulated and dry-mixed with the other components of the hot-melt adhesive composition and the composition heated in a mixer until the hydroxy-functionalized polyether is melted to form a flowable mixture. This flowable mixture can then be subjected to a shear in a mixer sufficient to form the desired composition. The hydroxy-functionalized polyether may also be heated in the mixer to form a flowable mixture prior to the addition of the other components of the hot-melt adhesive composition. The hydroxy-functionalized polyether and the other components are then subjected to a shear sufficient to form the desired hot-melt adhesive composition.

The superabsorbent water-swellable or lightly cross-linked hydrophilic polymers suitably employable in the present invention can be any of the known hydrophilic polymers which are capable of absorbing large quantities of fluids. These polymers are well known in the art and are widely commercially available.

Examples of some suitable polymers and processes, including gel polymerization processes, for preparing super-absorbent polymers are disclosed in U.S. Pat. Nos. 3,997,484; 3,926,891; 3,935,099; 4,090,013; 4,093,776; 4,340,706; 4,446,261; 4,683,274; 4,459,396; 4,708,997; 4,076,663; 4,190,562; 4,286,082; 4,857,610; 4,985,518; and 5,145,906, which are incorporated herein by reference. In addition, see Buchholz, F. L. and Graham, A. T., "Modern Superabsorbent Polymer Technology," John Wiley & Sons (1998). Preferred hydrophilic polymers are prepared from water-soluble $\alpha,\beta$-ethylenically unsaturated monomers such as monocarboxylic acids, polycarboxylic acids, acrylamide and their derivatives.

The superabsorbent compositions of this invention are useful in the manufacture of moisture absorbent articles, such as disposable diapers, sanitary napkins, incontinence garments and bandages. For example, the superabsorbent polymers of this invention can be used in the manufacture of absorbent articles such as those described in U.S. Pat. Nos. 3,669,103; 3,670,731; 4,654,039; 4,430,086; 4,973,325; 4,892,598; 4,798,603; 4,500,315; 4,596,567; 4,676,784; 4,938,756; 4,537,590; 4,673,402; 5,061,259; 5,147,343; and 5,149,335; the teachings of which are hereby incorporated by reference. See also EP 0 719 531 A1, and WO 98/51251. Construction of diapers and other absorbent articles is well known, and materials useful as fluff in absorbent articles are also well known. See, for example, U.S. Pat. No. 4,795,454. For the purposes of the present invention, the term "fluff" is given its meaning as understood by those of ordinary skill in the art. Examples of fluff include cotton fibers, curly fibers, wood pulp fibers, synthetic fibers, or a combination thereof, which can be formed into a pad and absorb primarily by capillary attraction mechanism. See, e.g., U.S. Pat. No. 4,610,678.

In making absorbent articles with the compositions of this invention, the superabsorbent composition may be mixed with, attached to, layered in, or dispersed in a porous matrix of fibers. Such matrices, or substrates, are made with fibers such as wood pulp or fluff, cotton linters, and synthetic fibers or a mixture of the fibers and the wood fluff. The fibers preferably are hydrophilic. The fibers can be loose or joined as in nonwovens. Examples of synthetic fibers include those made using polyethylene, the hydroxy-functionalized polyether component of the invention, polypropylene, polyesters, and copolymers of polyesters and polyamides. The synthetic fibers may be meltblown fibers or fibers which have been treated to render them hydrophilic.

Absorbent articles may be constructed by a variety of processes known in the art. In general, natural or synthetic fibers are fluidized in a stream of water or air; those skilled in the art refer to a "wet-laid" process when water is employed and to an "air-laid" process when air is employed. Superabsorbent polymers and other particles, such as the polyether in particulate form, may be included in this fluidized mixture. The fluidized mixture is then formed into a web by depositing said mixture onto a perforated surface to separate the solids from the fluid. The perforated surface may be covered with tissue or other fabric to improve the solids/fluid separation efficiency. Superabsorbent polymers and other particles may also be added to the surface of the pre-formed web. Additional layers, which may be added to the initial layer, may contain different fibers and different particles.

Examples of multi-compartmentalized or multi-layered structures are described in U.S. Pat. Nos. 4,338,371; 4,935,022; 5,364,382; 5,429,629; 5,486,166; 5,520,673; 5,531,728; 5,562,646; and 5,728,082, the teachings of which are incorporated herein by reference. See also WO patent application numbers 91/11163, 92/11831, 95/00183, 95/01146, 95/22358, 95/26209, 97/12575, 97/13484, 97/34558, 98/06364, 98/22065, 98/22066, and 98/22067. See also the following EP publication numbers: 401 189, 558 889, 640 330 and 670 154, as well as FR-A-2,627,080.

Cable wrap that employs superabsorbent polymer is also well known to those skilled in the art, as are the methods for preparation of cable wrap. The compositions of this invention are also useful in the manufacture of water-blocking components in electrical and telecommunication cables. The substrate material for these water-blocking components can be films, tapes, or strands of natural or synthetic materials. The superabsorbent polymer composition can be incorporated into or onto these substrates using a variety of methods known in the art. The superabsorbent polymer-containing substrate is then wrapped around a bundle of individual wires or fibers. Superabsorbents may also be adhered directly to individual wires or fibers in electrical or telecommunication cables using a variety of methods known in the art.

The absorbent articles of the invention may comprise from 5 percent to 95 percent by weight of the superabsorbent/hydroxy-functionalized polyether compositions of the invention based on the weight of the article. In a typical absorbent article, the superabsorbent/hydroxy-functionalized polyether composition of the invention may be dispersed in a fiber matrix in which the superabsorbent/hydroxy-functionalized polyether composition of the invention is present in an amount from 30 to 70 weight percent and the fiber matrix comprises 70 to 30 weight percent of the article; preferably, the superabsorbent/hydroxy-functionalized polyether composition of the invention is dispersed in a fiber matrix in which the superabsorbent/hydroxy-functionalized polyether composition of the invention is present in an amount from 15 to 85 weight percent and the fiber matrix comprises 85 to 15 weight percent of the article. In another form of absorbent article, the superabsorbent may be present in a containment structure in which the superabsorbent/hydroxy-functionalized polyether composition of the invention is present in an amount of 30 to 95 percent by weight. In the preparation of absorbent articles it is possible to employ the superabsorbent/hydroxy-functionalized polyether composition of the invention as a material homogeneously dispersed in the fiber matrix, as a material contained in layers or pockets in the fiber matrix, or both.

SPECIFIC EMBODIMENTS OF THE INVENTION

The following examples and comparative experiments are given to illustrate the invention and should not be construed as limiting its scope. All parts and percentages are by weight unless otherwise indicated. The following test methods were employed unless otherwise indicated: MFI test: ASTM D1238-95; Tenacity: ASTM D3822-96; and Denier (Linear Density): ASTM D1577-96

The following abbreviations are used in the examples: SAP: superabsorbent polymer; HFPE: hydroxy-functionalized polyether; PHAE: (poly(hydroxy amino ether)); PHEE: (poly(hydroxy ester ether)); and PKHH: (phenoxy resin).

Construction Methods 1, 2 and 3 are examples of methods that can be used to produce an absorbent article or a portion of an absorbent article. The SAP employed for all examples and comparative experiments is DRYTECH 2015M brand superabsorbent polymer, which is available from The Dow Chemical Company.

CONSTRUCTION METHOD 1—LAYERED DESIGN

This pad construction method makes a pad having a layered design on a diaper pad former designed to simulate full-scale diaper production. Fluff pulp (11.6 grams) is dispersed in an air stream. This solid/air mixture is passed across a layer of tissue supported by a perforated surface to separate the solids from the air and create a layer of fluff that is substantially uniform in thickness. The fluff pulp layer is then split in the thickness direction. A mixture of 8.5 grams of SAP and varying amounts of PHEE is then added uniformly to the surface of one of the fluff layers. The other fluff layer is then placed on top of the fluff/SAP/PHEE layer. This layered composite is then wrapped in tissue and pressed for between 60 and 180 seconds to a thickness of 1.59 mm between plates that are heated to the desired temperature.

CONSTRUCTION METHOD 2—HOMOGENEOUS DESIGN

This pad construction method makes a pad of homogeneous design on a diaper pad former designed to simulate full-scale diaper production. Fluff pulp (11.6 grams) and a SAP/HFPE mixture is dispersed in an air stream. This solid/air mixture is passed across a layer of tissue supported by a perforated surface to separate the solids from the air and create a layer of fluff, SAP and HFPE that is substantially uniform in thickness and is a substantially homogeneous mixture of the solid components. The SAP/HFPE mixture is made using 8.5 grams of SAP and varying amounts of HFPE. This 5 homogeneous composite is then wrapped in tissue and pressed for 2–10 seconds to a thickness of 1.59–3.18 mm between plates that are heated to the desired temperature.

DISINTEGRATION METHOD 1

The composite pads are disintegrated by manually tearing the pads into approximately 1/8" diameter pieces. Some SAP particles fall free from the pad fragments during the tearing process. Some other SAP particles are located by touch and, if free to move, are then picked from the fluff of the pad fragments. Both categories of loose particles are collected and weighed. The "Shakeout %" is the mass of collected SAP particles divided by the mass of SAP used in producing the composite pad multiplied by 100.

DISINTEGRATION METHOD 2

The composite pads are disintegrated by manually tearing them into approximately 1" diameter pieces and placing them in a Waring blender. These pieces are blended at the high setting for 3 seconds. The blended composite is placed in the top of a screen stack of progressively finer U.S. sieve series screens. The top screen is 14 mesh (1410 microns), the middle screen is 50 mesh (297 microns), and the bottom screen is 170 mesh (88 microns). Particles are then separated from fluff by agitating the screen stack for 10 minutes. Agitation of the screen stack is accomplished with a Ro-Tap testing sieve shaker (manufactured by W. S. Tyler, Inc.). The screened fluff is then separated, loose particles are collected and removed from the screen set, and the fluff is screened again; then, this procedure is repeated one more time. After the three screening steps, the collected SAP particles are combined and screened one final time and collected. The "Shakeout %" is the mass of collected SAP particles divided by the mass of SAP used in producing the composite pad multiplied by 100.

COMPARATIVE EXAMPLE A AND EXAMPLES 1–3

A PHEE polyether was employed as the HFPE. More specifically, a poly(hydroxyesterether) that is based on formula VII, that has a weight average molecular weight of 20,000 g/mole, and that is the reaction product of the diglycidyl ether of bisphenol A and adipic acid, was employed. The PHEE polyether was ground and screened using a 140 mesh (105 micron) screen, and the particles that passed through the screen were employed in the construction of composite pads according to Construction Method 1 with a press temperature of 100° C. The composite pad was then torn apart (manually disintegrated) using Disintegration Method 1. The particles that were unattached to fluff and therefore able to be separated from the fluff by hand were termed "recovered." The percentage of recovered SAP based on the amount used to construct the composite is shown in Table 1 below for various amounts of added PHEE. High values of SAP retention and low values of recovered SAP are desirable.

TABLE 1

Amount of PHEE used versus Shake-out

| Example No. | Construction Method | Disintegration Method | PHEE Amount (grams) | Press Time (seconds) | Percent of SAP Recovered (Shake-out %) |
| --- | --- | --- | --- | --- | --- |
| Comparative Example A | 1 | 1 | 0 | 120 | 90% |
| Example 1 | 11 | 1 | 0.0085 | 60 | 53% |
| Example 2 | 1 | 1 | 0.085 | 180 | 1.1% |
| Example 3 | 1 | 1 | 0.85 | 120 | 0% |

COMPARATIVE EXAMPLE B AND EXAMPLES 4–5

The method of Example 2 was repeated except that the composite pads were formed using Construction Method 2, and heating times were varied.

TABLE 2

Press Time vs. Shake-out

| Example No. | Construction Method | Disintegration Method | PHEE Amount (grams) | Press Time (seconds) | Percent of SAP Recovered (Shake-out %) |
| --- | --- | --- | --- | --- | --- |
| Comparative Example B | 2 | 1 | 0 | 10 | 13.4% |
| Example 4 | 2 | 1 | 0.085 | 10 | 0.1% |
| Example 5 | 2 | 1 | 0.085 | 2 | 2.4% |

The results in Tables 1 and 2 demonstrate that including from 0.1 to 10% PHEE, based on SAP, improves SAP retention (decreases the Shake-out %) in both layered and homogeneous pads.

COMPARATIVE EXAMPLE C AND EXAMPLES 6–7

A group of composite pads were constructed using Construction Method 2. The HFPE polymer was a PHAE, i.e. a poly(hydroxyaminoether), based on formula II, that was the reaction product of the diglycidyl ether of bisphenol A and monoethanolamine. The PHAE had a Melt Flow Index of 3, measured at 190 C using a 2.16 kg weight. The PHAE was ground and screened using a 140 mesh (105 micron) screen, and the particles that passed through the screen were employed. The composite pads were disintegrated using Disintegration Method 2. The percentage of recovered SAP based on amount used to construct the composite is shown in Table 4 for different press times and temperatures:

TABLE 4

Examples with PHAE

| Example No. | Construction Method | Disintegration Method | PHAE Amount (grams) | Press Time (seconds) | Press Temp (° C.) | Percent of SAP Recovered (Shake-out %) |
|---|---|---|---|---|---|---|
| Comparative Example C | 2 | 2 | 0 | 10 | 100 | 79% |
| Example 6 | 2 | 2 | 0.085 | 10 | 100 | 79% |
| Example 7 | 2 | 2 | 0.085 | 80 | 135 | 42% |

Although Example 6 shows no improvement in Shake-out % compared to Comparative Example C, Example 7 shows that increasing the press heating time and temperature yields significantly reduced Shake-out % and improved SAP retention.

composite was subjected to Disintegration Method 2. The press time and temperature are those of Example 7. The Shake-out % was 60% compared to 42% for Example 7. These results show that the HFPE can be employed either as a granule or as a chopped fiber.

EXAMPLE 9

The method of Example 7 was repeated except that a PHAE with a higher melt flow index (MFI) (8 instead of 3) was employed. The PHAE, was based on formula II, and was the reaction product of the diglycidyl ether of bisphenol A and monoethanolamine. The PHAE had a Melt Flow Index of 8, measured at 190 C using a 2.16 kg weight. The percentage of recovered SAP based on the amount used to construct the composites is shown in Table 6.

TABLE 6

Variations in Melt Flow Index

| Example No. | HFPE Type | Construction Method | Disintegration Method | HFPE Amount (grams) | Press Time (seconds) | Press Temp (° C.) | Percent of SAP Recovered (Shake-out %) |
|---|---|---|---|---|---|---|---|
| Comparative Example C | None | 2 | 2 | 0 | 10 | 100 | 79% |
| Example 7 | PHAE (MFI = 3) | 2 | 2 | 0.085 | 80 | 135 | 42% |
| Example 9 | PHAE (MFI = 8) | 2 | 2 | 0.085 | 80 | 135 | 35% |

EXAMPLE 8

A bi-component fiber composed of 30% PHAE and 70% polypropylene was chopped into pieces 1 mm in length. The fiber had 288 filaments and a core/sheath geometry. The PHAE had a MFI of 20, and the polypropylene had a MFI of 35. The fiber had a denier of 6.7 DPF and a Tenacity of 0.74. A composite was constructed using 0.2805 gram of this fiber as the source of HFPE in Construction Method 2. The These results show that the Shake-out values may be optimized by taking into account the properties (melt flow index or molecular structure) of the HFPE binder.

EXAMPLES 10–11

A group of composite pads was constructed using Construction Method 2 using the PHAE of Example 6. Each pad was draped over a 2 cm diameter rod to evaluate stiffness. A horizontal measurement was made of the distance between the two inner surfaces of each pad 5 cm below the fold in the pad. The composites were rated, and the ratings are listed in Table 7, using the following ratings:

TABLE 7

Composite Pad Stiffness

| Example No. | HFPE Type | Construction Method | HFPE Amount (grams) | Press Time (seconds) | Press Temp (° C.) | Stiffness Rating |
|---|---|---|---|---|---|---|
| Comparative Example D | None | 2 | 0 | 80 | 135 | + |
| Example 10 | PHAE | 2 | 0.085 | 80 | 135 | + |
| Example 11 | PHAE | 2 | 0.85 | 80 | 135 | ± |

+ very supple (horizontal distance < 7 cm)
± slightly stiff (horizontal distance 7–8 cm)
− very stiff (horizontal distance > 8 cm)

EXAMPLE 12

The method of Example 7 was repeated except that PKHH was employed as the HFPE. The PKHH was a poly(hydroxyether) based on formula I, and was the reaction product of bisphenol A and the diglycidyl ether of bisphenol A. The PKHH had a Melt Flow Index of 8, measured at 190 C using a 2.16 kg weight. The percentage of recovered SAP based on the amount of SAP used to construct the composite is shown in Table 8.

TABLE 8

Variations in Pressing Conditions

| Example No. | HFPE Type | Construction Method | Disintegration Method | PKHH Amount (grams) | Press Time (seconds) | Press Temp (° C.) | Percent of SAP Recovered (Shake-out %) |
|---|---|---|---|---|---|---|---|
| Example 12 | PKHH | 2 | 2 | 0.085 | 80 | 135 | 18% |

CONSTRUCTION METHOD 3—WITH PHEE LATEX

This pad construction method makes a pad of homogeneous design on a diaper pad former designed to simulate full-scale diaper production. Fluff pulp (11.6 grams) and SAP (8.5 grams) were dispersed in an air stream. This solid/air mixture was passed across a layer of tissue supported by a perforated surface to separate the solids from the air and create a layer of fluff and SAP that is substantially uniform in thickness and was a substantially homogeneous mixture of the solid components. With the tissue still not folded over the homogeneous composite the top of the pad was evenly sprayed with 9 grams of the PHEE latex. The pad was dried at 40° C. for 6 hr. The cover sheet was folded around the composite before the pad was pressed at 100° C. for 20 sec.

EXAMPLE 13 AND COMPARATIVE EXAMPLE E

A PHEE, more specifically a poly(hydroxyesterether) based on formula VII, with a weight average molecular weight of 55,000 g/mole and that was the reaction product of adipic acid and D.E.R. 331 brand epoxy resin (available from The Dow Chemical Company), was made into a PHEE latex using the method of WO 99/12995 (published Mar. 18, 1999) using the surfactant used in Example 1 of that publication. The PHEE-latex had 50.7% solids, a particle size of 1.03 μm and a surfactant concentration of 3.7%. Prior to use in Construction Method 3, the -latex was diluted with 2.5 parts water per part of the 47% PHEE-latex.

(Spray mass) (Dilution) (%)=(9 g PHEE)×(1/2.5)×(0.47)= 1.69 g PHEE which is 1.69g PHEE/8.5grams superabsorbent polymer=19.91% active PHEE.

The comparative pad of Comparative Example E was constructed using the same procedure except that no PHEE latex was employed.

TABLE 9

PHEE-latex

| Example No. | HFPE Type | Construction Method | Disintegration Method | HFPE Amount (grams) | Press Time (seconds) | Press Temp (° C.) | % SAP Recovered (Shake-out %) |
|---|---|---|---|---|---|---|---|
| Comparative Example E | None | 3 | 2 | 0 | 20 | 100 | 57 |
| Example 13 | PHEE-latex | 3 | 2 | 1.69 | 20 | 100 | 37 |

These results show that the use of PHEE in the form of a latex improves SAP retention (decreases the Shake-out %).

What is claimed is:

1. A composition comprising: (a) a superabsorbent polymer comprising at least one polytnaized monomer selected from the group consisting of a carboxylic acid, acrylamide, or derivatives thereof, and (b) a binding amount of a hydroxy-functionalized polyeher.

2. The composition of claim 1 wherein the hydroxy-functionalized polyether has a multimodal molecular weight distribution or is a mixture of two or more hydroxy-functionalized polyethers having different molecular weights.

3. The composition of claim 1 wherein the hydroxy-functionalized polyether is a poly(hydroxy ether) having repeating units represented by the formula:

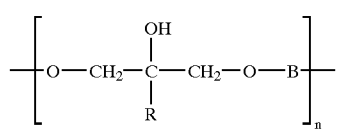

I wherein B is a divalent organic moiety which is predominantly hydrocarbylene, each R independently is alkyl or hydrogen, and n is an integer from 5 to 1000.

4. The composition of claim 3 wherein the hydroxy-functionalized polyether is prepared by the reaction of a diglycidylether or epihalohydrin with a bisphenol.

5. The composition of claim 1 wherein the hydroxy-functionalized polyether is a poly(hydroxy amino ether) having repeating units represented by the formula:

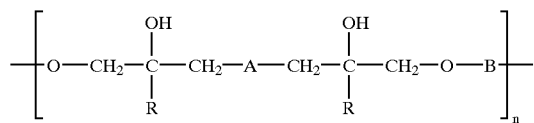

II wherein A is a diamino moiety or a combination of different amine moieties; B is a divalent organic moiety which is predominantly hydrocarbylene; each R independently is alkyl or hydrogen; and n is an integer from 5 to 1000.

6. The composition of claim 5 wherein the hydroxy-functionalized polyether is prepared by the reaction of a diglycidyl ether with a difunctional amine.

7. The composition of claim 1 wherein the hydroxy-functionalized polyether is a poly(hydroxy ether sulfonamide) having repeating units represented by any one of the formulas:

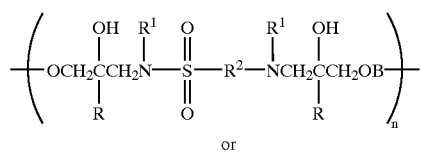

IIIa or

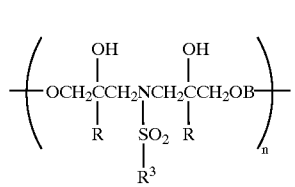

IIIb wherein each R independently is hydrogen or alkyl, $R^1$ and $R^3$ are independently a substituted or an unsubstituted alkyl or aryl wherein the substituent(s) is a monovalent moiety which is inert in the reactions used to prepare the hydroxy-functionalized polyether; B and $R^2$ are independently a divalent organic moiety which is predominantly hydrocarbylene, and n is an integer from 5 to 1000.

8. The composition of claim 7 wherein the hydroxy-functionalized polyether is prepared by the reaction of a diglycidyl ether and a difunctional sulfonamide.

9. The composition of claim 1 wherein the hydroxy-functionalized polyether is a poly(hydroxy-ether sulfide) that has repeating units represented by the formula:

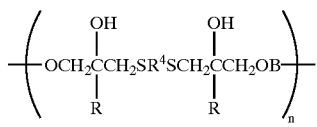

IV wherein each R independentlyis hydrogen or alkyl, $R^4$ and B are independently a divalent organic moiety which is predominantly hydrocarbylene and n is an integer from 5 to 1000.

10. The composition of claim 9 wherein the hydroxy-functionalized polyether is prepared by the reaction of a diglycidyl ether and a dithiol.

11. The composition of claim 1 wherein the hydroxy-functionalized polyether is a poly(hydroxy amide ether) having repeating units represented independently by any one of the formulas:

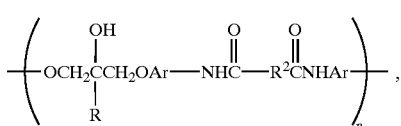

Va

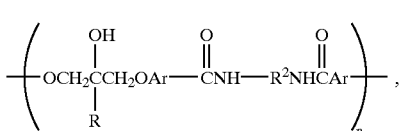

Vb or

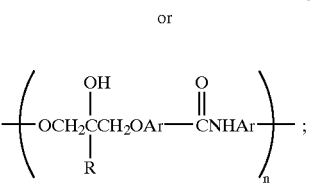

Vc or a poly(hydroxy amide ether) having repeating units represented by any one of the formulas:

VIa

VIb or

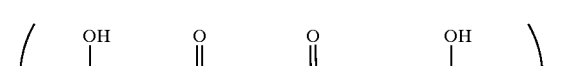

-continued

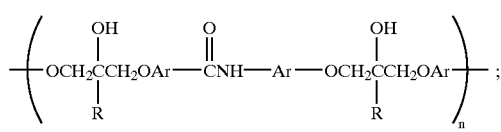
VIc wherein each R independently is hydrogen or alkyl, $R^2$ and Ar are independently a divalent organic moiety which is predominantly hydrocarbylene, and n is an integer from 5 to 1000.

12. The composition of claim 1 wherein the polyether is employed as part of a hot melt adhesive composition, optionally comprising a compatible tackifier, a compatible plasticizer and a compatible diluent.

13. The composition of claim 12 wherein the tackifier is a terpene phenolic resin or a benzoate or a mixture thereof in an amount of from 0 to 90 percent by weight.

14. The composition of claim 12 wherein the plasticizer is a phthalate plasticizer, benzoate plasticizer, a liquid polyester, a phosphate plasticizer, a polyalkylene glycol, a vegetable oil, or an animal oil in an amount of from 0 to 90 percent by weight.

15. The composition of claim 12 wherein the diluent is a wax in an amount of from 0 to 50 percent by weight.

16. The composition of claim 15 wherein the wax is N-(2-hydroxyethyl)-12-hydroxystearamide wax, hydrogenated castor oil or an oxidized synthetic wax.

17. The composition of claim 1 wherein component (b) is present in an amount of from 0.01 to 20 weight percent based on the weight of the composition.

18. The composition of claim 17 wherein component (b) is present in an amount of from 0.15 percent to 4 percent.

19. The composition of claim 17 wherein component (b) is present in an amount of from 0.25 percent to 2 percent.

20. The composition of claim 1 wherein the hydroxy-functionalized polyether is a poly(hydroxy ester ether) or poly(hydroxy ester) having repeating units represented by the formula:

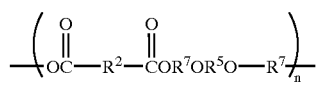
VII wherein $R^5$ is

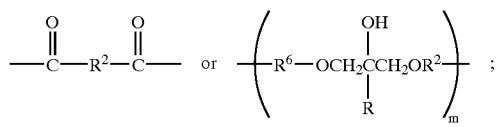

$R^6$ is a divalent organic moiety which is predominantly hydrocarbylene or

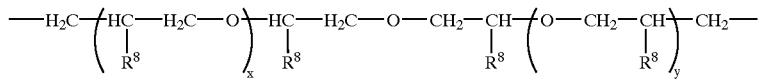

$R^7$ is

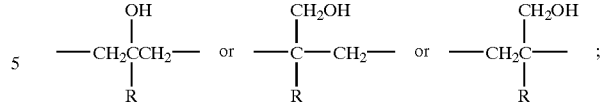

each R independently is alkyl or hydrogen; each $R^2$ is independently a divalent organic moiety which is predominantly hydrocarbylene; each $R^8$ independently is methyl or hydrogen; m and y are each independently from 0 to 100; and n is an integer from 5 to 1000.

21. The composition of claim 1 wherein the polyether is not the reaction product of a dicarboxylic acid with a diglycidyl ether.

22. The composition of claim 1 wherein the polyether is thermoplastic.

23. An absorbent article comprising the composition of claim 1.

24. The composition of claim 1 further comprising at least one fiber.

25. The composition of claim 1 further comprising a cellulosic material.

26. The composition of claim 1 wherein the hydroxy-functionalized polyether is in particulate form and has a weight average particle diameter of from 10 to 200 microns.

27. The composition of claim 1 wherein the hydroxy-functionalized polyether is in particulate form and has a weight average particle diameter of from 50 to 150 microns.

28. A process comprising contacting a substrate with (a) a superabsorbent polymer comprising at least one polymerized monomer selected from the group consisting of a carboxylic acid, acrylamide, or derivatives thereof, and (b) a binding amount of a hydroxy-functionalizd polyether.

29. The process of claim 28 wherein the substrate comprises a cellulosic material.

30. The process of claim 28 wherein the polyether is thermoplastic.

31. The process of claim 28 wherein the amount of polyether is from 0.01 percent to 20 percent, based on the total weight of polyether and superabsorbent polymer.

32. The process of claim 28 wherein the amount of polyether is from 0.1 percent to about 10 percent, based on the total weight of polyether and superabsorbent polymer.

33. The process of claim 28 wherein the amount of polyether is from 0.25 percent to 2 percent, based on the total weight of polyether and superabsorbent polymer.

34. An absorbent article prepared using the process of claim 28.

35. The process of claim 28 wherein the polyether is a component of a hot melt adhesive composition which further optionally comprises a compatible tackifier, a compatible plasticizerand a compatible diluent.

36. A process for preparng an absorbent article comprising a superabsorbent polymer and cellulose-containing fluff, the process comprising contacting at least a portion of the fluff with a binding amount of a hydroxy-functionalized polyether and with a superabsorbent polymer, the superabsorbent polymer comprising at least one polymerized monomer selected from the group consisting of a carboxylic acid, acrylamide, or derivatives thereof; in such a manner that an absorbent article is formed.

37. The process of claim 36 wherein an air-laid process is employed.

38. The process of claim 36 wherein a wet-laid process is employed.

39. The composition of claim 1 wherein the superabsorbent polymer comprises polymerized acrylic acid.

* * * * *